United States Patent [19]

Torzala

[11] 4,121,578

[45] Oct. 24, 1978

[54] PHYSIOLOGICAL RESPONSIVE CONTROL FOR AN OXYGEN REGULATOR

[75] Inventor: Terence August Torzala, Davenport, Iowa

[73] Assignee: The Bendix Corporation, Southfield, Mich.

[21] Appl. No.: 729,580

[22] Filed: Oct. 4, 1976

[51] Int. Cl.² ............................................. A61M 16/00
[52] U.S. Cl. ...................... 128/142 R; 128/DIG. 29; 137/81
[58] Field of Search ............. 128/142 R, 142.2, 145.8, 128/DIG. 17, DIG. 29, 209, 210, 191 R, 145.6; 137/81, 88

[56] References Cited

U.S. PATENT DOCUMENTS 3,957,043   5/1976   Shelby ............................. 128/191 R

FOREIGN PATENT DOCUMENTS 459,242   4/1975   U.S.S.R. ............................. 128/142 R

OTHER PUBLICATIONS

Mitamura et al., "An Optimally Controlled Respirator", Sep. 1971, IEEE Transactions on Bio-Medical Engr. BME-18, No. 5, pp. 330–337.

*Primary Examiner*—Henry J. Recla
*Attorney, Agent, or Firm*—Leo H. McCormick, Jr.; Ken C. Decker

[57] ABSTRACT

A control mechanism for regulating the proportion of a first and second fluid in a breathable fluid by measuring the physiological needs associated with the instantaneous operational parameter of an individual recipient.

2 Claims, 1 Drawing Figure

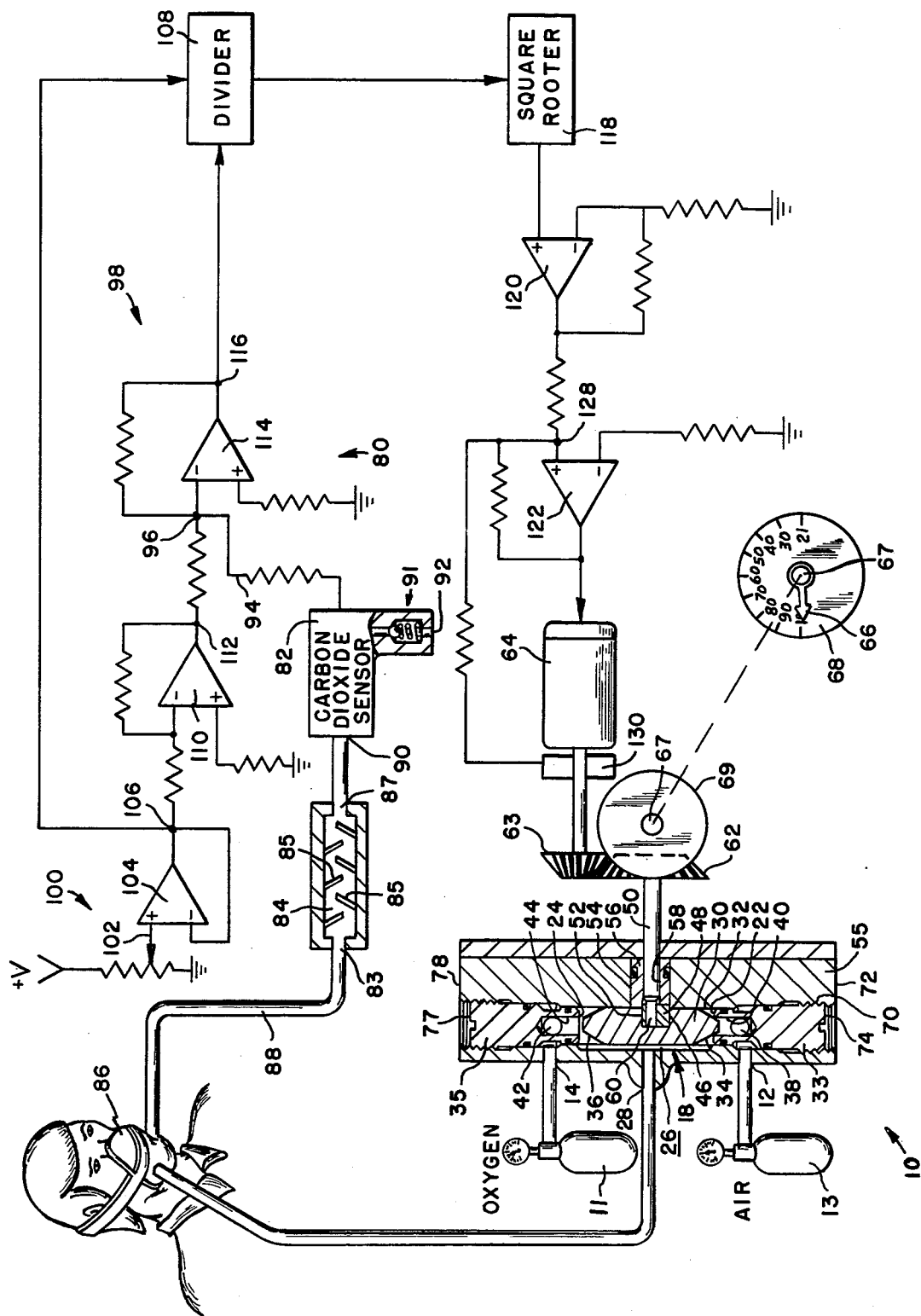

PHYSIOLOGICAL RESPONSIVE CONTROL FOR AN OXYGEN REGULATOR

BACKGROUND OF THE INVENTION

This invention relates to an oxygen regulator for use in an aircraft.

Currently available demand oxygen regulators such as that disclosed in U.S. Pat. No. 3,509,895 supply a recipient with a mixture of breathable fluid which is directly proportional to the altitude at which the aircraft is flying. However, each individual's physiological response to various stresses encountered during a flight is different. Depending upon the individual, during periods of increased work levels, an increase in the percentage of the oxygen in the breathable fluid may be needed to stabilize minute ventilation of blood gases. If the percentage of oxygen is not increased, the recipient's body responds by automatically increasing his inhalation-exhalation rate and/or tidal volume in order that the waste products produced by the body may be eliminated by bringing more oxygen into the lungs. However, under such conditions, hyperventilation can occur since the efficiency of respiration is decreased due to an increase in the work of breathing.

In addition, during periods of inactivity the percentage of oxygen in the breathable fluid needed to stabilize minute ventilation of blood gases in an individual recipient may be less than that supplied by the altitude responsive regulator. If the percentage of oxygen is not reduced, the recipient may experience hyperoxia.

SUMMARY OF THE INVENTION

In order to stabilize minute ventilation and to prevent hyperventilation and/or hyperoxia which a recipient of an altitude responsive oxygen regulator can experience, I discovered that a feedback signal indicative of a recipient's physiological oxygen needs may be used to operate an oxygen regulator. A recipient's physiological oxygen needs can be measured by determining the amount of inspired oxygen utilized during each breath and comparing the same with a reference for the recipient.

A recipient's average physiological dead space volume ($\bar{V}_D$) to to tidal volume ($\bar{V}_T$) ratio is a good indication of oxygen utilization. The physiological dead space volume can be determined by solving Bohr's equation relating to the partial pressure of a component in a gas. The recipient's exhaled fluid is communicated into a mixing chamber where a carbon dioxide analyzer determines the mean partial pressure of the carbon dioxide in the exhaled fluid to produce a signal representative of the utilization of oxygen by the recipient. The utilization signal is communicated to a comparator and compared with a reference signal representing the normal utilization of oxygen by the recipient to produce an operational signal. The operational signal is communicated to a servomotor which is connected to a proportioning valve in an oxygen regulator. If the utilization signal is greater than the reference signal, the operational signal supplies the servomotor with a driving force to allow a larger percentage of oxygen in the breathable fluid. If the utilization signal is less than the reference signal, the operational signal supplies the servomotor with a driving force to reduce the percentage of oxygen in the breathable fluid. When the utilization signal and the reference are equal, the servomotor is deactivated and the percentage of oxygen in the breathable fluid remains stationary even though the aircraft may change altitude.

It is the object of this invention to provide an oxygen regulator with a control means responsive to the physiological needs of a recipient for establishing the proportion of oxygen in a breathable fluid.

It is another object of this invention to provide an oxygen regulator with a physiological feedback signal for controlling the percentage of oxygen in a breathable fluid.

It is another object of this invention to provide an oxygen regulator with a servomotor which is responsive to a physiological signal for proportioning the percentage of oxygen in a breathable fluid.

These and other objects will become apparent from reading this specification and viewing the drawings.

BRIEF DESCRIPTION OF THE DRAWING

The drawing is a schematic illustration of a control means, constructed according to the principles of this invention, for operating an oxygen regulator in response to the physiological needs of a recipient.

DETAILED DESCRIPTION OF THE EMBODIMENT

In the drawing, an oxygen regulator 10 has a first inlet port 12 connected to a source of air and a second inlet 14 connected to a source of oxygen. The oxygen regulator 10 has control valves therein which are simultaneously operated by an inhalation demand of a recipient in a manner completely described in U.S. Pat. No. 3,693,653 which is incorporated herein by reference. A proportioning valve 18 controls the percentage of air and oxygen delivered through orifices 22 and 24 into the mixing chamber 26 for distribution to a recipient through the outlet port 28.

The proportioning valve 18 has a cylindrical body 30 which is slidable in bore 32 with a first face 34 and a second face 36 aligned with seats surrounding orifices 22 and 24, respectively, in the first and second closure caps 33 and 35. The first closure cap 33 has a cross bore 38 and an axial bore 40 which connect the mixing chamber 26 with the air supply flow chamber in the oxygen regulator. The second closure cap 35 has a cross bore 42 and an axial bore 44 which connect the mixing chamber 26 with the oxygen supply flow chamber (not shown) in the oxygen regulator. A shaft 50 is connected to the cylindrical body 30 for locating the first and second faces 34 and 36 in bore 32 with respect to seats surrounding orifices 22 and 24.

The cylindrical body 30 has a slot 46 located between the first and second faces 34 and 36 for retaining a cylindrical roller 48. The roller 48 has a keyway 52 eccentrically located with respect to the axial center of the roller 48. The roller 48 which extends into bore 54 of the housing 55 of the oxygen regulator abuts bearing member 56. The bearing member 56 has an axial bore 58 for holding shaft 50 in axial alignment within bore 54. The end 60 of shaft 50 has an irregular shape, such as a square, which is located in keyway 52 for rotating roller 48 as gear 62 on shaft 50 is driven by motor 64.

A pointer 66 driven by gear 69 on shaft 67 is located over indicator dial 68 attached to the housing of the proportioning valve 18 to provide a visual indication of the percentage of oxygen in the breathing fluid.

When the pointer 66 indicates 100 percent, oxygen is being communicated into the mixing chamber 26, the first face 34 is positioned on seat 22. In order to assure that face 34 is positioned on seat 22, closure cap 33 is adjusted by screwing threads 70 to change the position of end 74 with respect to slide 72 of housing 55.

When pointer 66 indicates 21 percent oxygen is being communicated into the mixing chamber 26, the second face 36 is positioned on seat 24. To assure that face 36 and seat 24 are engaged, end cap 35 is adjusted by screwing threads 76 to change the position of end 77 with respect to side 78 of housing 55.

Movement of the pointer 66 between the 21 percent to the 100 percent oxygen position is controlled by an operational signal supplied motor 64 by the physiological control 80. The physiological control 80 monitors oxygen utilization of the recipient by measuring the carbon dioxide content in each breath of expired air. In order to prevent erratic measurements by a carbon dioxide sensor 82 in the physiological control 80, the expired air of the recipient is communicated from a face mask 86 through conduit 88 and into a mixing chamber 84 to establish a mean for the carbon dioxide level over a fixed time period before being communicated into the carbon dioxide sensor 82 through inlet 90. A one-way check valve 91 is located in the exit port 92 of sensor 82 of prevent ambient air from diluting the means concentration level of carbon dioxide communicated from the mixing chamber 84.

The carbon dioxide sensor 82 can be any well known analyzer which has the capability of providing an accurate analysis of the percentage of carbon dioxide in a fluid mixture within a time period of one minute. The carbon dioxide sensor 82 is utilized to measure the percentage of carbon dioxide in the means sample to develop a mean partial pressure signal representative of the partial pressure of carbon dioxide in the fluid mixture.

The mean partial pressure signal is carried on lead 94 to a summing junction 96 in the computer section 98 of the physiological control means 80.

The physiological control 80 compares the mean carbon dioxide partial pressure signal with a reference partial carbon dioxide pressure. The mean reference partial pressure is derived from the arterial carbon dioxide partial pressure for the recipient. The physiological control 80 establishes an operational signal for controlling the percentage of oxygen delivered to the recipient by the regulator means 10.

To establish the operational signal, the physiological control 80 must establish the relation of oxygen to carbon dioxide in expired air of the recipient by solving the following equations:

$$F_1O_2 \frac{(RV_D/\bar{V}_T)}{(V_D/\bar{V}_T)} \quad (1)$$

where:
$F_1O_2$ = fractional concentration of $O_2$
$RF_1O_2$ = fractional concentration of $O_2$ determination at atmospheric pressure — 0.21
$V_D$ = physiological dead space
$\bar{V}_T$ = mean tidal volume in which $V_D$ is measured
$RV_D/\bar{V}_T$ = ideal physiological ratio = 0.3

Making the appropriate substitutions, equation (1) is reduced to the following equation:

$$F_1O_2 = .21 \frac{(.03)}{(V_D/\bar{V}_T)} = .63 \frac{\bar{V}_T}{V_D} \quad (2)$$

It was determined by Danish physicist Niels H. D. Bohr that the physiological dead space $V_D$ could be determined through the measurement of the arterial partial pressure of carbon dioxide in blood gases. Bohr formulated the following equation (3) for determining physiological dead space:

$$V_D = \frac{(P_aCO_2 - P_e\overline{CO}_2)}{P_aCO_2} \bar{V}_T \quad (3)$$

where:
$P_aCO_2$ = partial pressure of arterial $CO_2$
$P_e\overline{CO}_2$ = partial pressure of mean mixed expired $CO_2$
$V_D$ = physiological dead space
$\bar{V}_T$ = average or mean tidal volume over which $P_e\overline{CO}_2$ is measured Substituting this relationship into the fractional concentration of oxygen equation (2) provides the following relationship:

$$F_1O_2 = \frac{kP_aCO_2}{P_aCO_2 - P_e\overline{CO}_2} \quad (4)$$

The partial pressure of the arterial carbon dioxide for a recipient is measured and used as a reference of normal oxygen utilization. The reference signal is introduced as an input to the physiological control 80 through an adjustable rheostat 100. The reference signal provides a norm whereby the partial pressure signal created in the carbon dioxide analyzer 82 is evaluated.

The reference signal which is introduced into the rheostat 100 varies for each individual recipient who uses the oxygen regulator since the normal physiological $V_D/\bar{V}_T$ of each individual is controlled by many parameters. However, each reference signal is communicated from the rheostat 100 to a voltage follower 104 through lead 102 to produce a positive reference signal at junction 106. The positive reference signal is simultaneously communicated to divider 108 and inverter amplifier 110. The inverter amplifier 110 changes the positive reference signal into a negative reference signal of the same magnitude at junction 112. The negative reference signal and the positive partial pressure signal are subtracted from each other in an inverter amplifier 114 to produce a utilization signal at junction 116. The utilization signal at junction 116 is positive since the inverter amplifier 114 algebraically combines the negative references signal with the positive partial pressure signal to produce a positive utilization signal. The positive utilization signal is carried to divider 108 to produce an operational signal.

It was found that the operational signal when directly supplied to the servomotor 64 produced sinusoidal movement in the proportional valve 18 and a modification or error signal was required to dampen the operational signal. Through experimentation, it was found that $V_D/\bar{V}_T$ be modified by the ratio of the $F_1O_2/RF_1O_2$. When the relationship is substituted into equation (1) a new equation (5) is produced as follows:

$$F_1O_2 = \frac{RF_1O_2 \, RV_D/V_T}{V_D/V_T(F_1O_2/RF_1O_2)} \quad (5)$$

solving equation (5) for $F_1O_2$, yields:

$$F_1O_2 = RF_1O_2 \frac{\sqrt{RV_D/V_T}}{V_D/V_T} \quad (6)$$

and when the arterial carbon dioxide pressures are substituted in equation (6) is reduced to the following:

$$F_1O_2 = k \frac{\sqrt{P_aCO_2}}{P_aCO_2 - P_e\overline{CO}_2} \quad (7)$$

Therefore, the operational signal from divider 108 is modified by a square rooter 118 to produce a servomotor activation signal. The servomotor activation signal is carried through an amplifier 120 where the ($k$) portion of equation (7) is introduced to the servomotor activation signal. The modified servomotor activation signal is then communicated to a summing junction 128. An output signal derived by measuring the rotational position of shaft 65 is transmitted from potentiometer 130 to the summing junction 128. When the output signal and the modified servomotor activation signal are equal, the oxygen in the breathing fluid supplied the recipient and his utilization are matched. However, any difference between the output signal and the modified servomotor activation signal is amplified by driver control 122 and supplied to servomotor 64 as an energization signal.

MODE OF OPERATION OF THE INVENTION

When a recipient desires to use the oxygen regulator 10, it is necessary to establish a reference level for arterial oxygen utilization. When the reference level is established for each individual, a corresponding reference signal is entered into the adjustable rheostat 100 to provide a basis for the normal requirements of oxygen for the individual. Thereafter, the face mask 86 is placed on the recipient and normal breathing is continued with air from the supply container 13 passing through inlet 12 into the mixing chamber 26. When the recipient inhales, breathable fluid flows from the mixing chamber 26 into mask 86. When the recipient exhales, the breathed air is communicated through conduit 88 into mixing chamber 84. The mixing chamber 84 has a series of baffles 85 to break up any direct communication between inlet 83 and outlet 87. The baffles 85 thoroughly mix each expired breath with a quantity of expired fluid representing several breaths retained in the mixing chamber 84 to provide a mean carbon dioxide sample. The mixed fluid is communicated from the outlet 87 into a sample chamber in the carbon dioxide analyzer 82. Thereafter, the exhaled fluid passes through the one-way check valve 91 to the surrounding atmosphere through port 92.

The carbon dioxide sensor or analyzer means 82 measures the mean amount of carbon dioxide in the exhaled air and create a partial pressure signal. The partial pressure signal is communicated to junction 96 by lead 94. During normal operation at ground level, the partial pressure signal and the reference signal are equal and the computer means 98 remains inactive.

However, with a change in altitude or an increase in work, the recipient is required to change his rate of breathing in order to remove waste from the lungs and supply the blood with oxygen to maintain physiological stability. With an increase in the amount of carbon dioxide in the exhaled or expired air, the carbon dioxide sensor 82 creates a partial pressure signal which is communicated to junction 96. Since the partial pressure signal is larger than the reference signal, a negative utilization signal is created and supplied the divider 108 to create a negative operational signal. The negative operational signal is modified by the square rooter 118 and amplifier 120 to provide driver 122 with an operational signal. The operational signal from the driver 122, is communicated to servomotor 64 which rotates gear 62 on shaft 50 by driver gear 63. When shaft 50 rotates, the eccentricity of keyways 52 causes surface 48 to rotate around bore 54; however, such movement provides valve 30 with linear motion to move face 36 away from seat 24 to allow oxygen from the supply container 11 to enter into the mixing chamber. After the fractional concentration of oxygen is increased in the breathable mixture supplied to the recipient, the minute ventilation of blood gases in the lungs correspondingly decreases. The decrease in minute ventilation, in response to an increase in the oxygen concentration, stabilizes as the partial pressure of the carbon dioxide in the expired breathed fluid matches the reference signal. With further changes in the work load of the recipient or in altitude of the aircraft, the utilization signal may need to be adjusted, and continues until such time that the oxygen regulator 10 is supplying 100 percent oxygen to the recipient.

However, with a decrease in the work load or a decrease in altitude, if the same percentage of oxygen is presented to the recipient, hyperventilation occurs. Because there is more oxygen presented to the recipient than is required to carry away the waste in the lungs, the percentage of carbon dioxide in each expired breath decreases. The utilization signal derived by the analyzer means 82 during such conditions is communicated to junction 96. In this case, the reference signal is larger than the partial pressure signal and a positive utilization signal is created. After the positive utilization signal is modified by divider 108, square rooter 118, and the ($k$) amplifier 120, a positive operational signal is supplied to the summing junction 128 and added to the position signal from the potentiometer 130. The resultant signal from the summing junction 130 is transmitted to the driver 122 and amplified to supply the servomotor 64 with an energization signal which rotates shaft 65. Rotation of shaft 65 moves shaft 50 to reduce the percentage of oxygen in the breathable fluid mixture presented to the recipient from chamber 26. The percentage of oxygen in the mixture is reduced until such time that the partial pressure signal is equal to the reference signal.

Through the control system 80, the oxygen regulator 10 is provided with a physiological responsive feedback signal to provide each recipient user thereof with adequate amount of oxygen enriched breathable fluid during work periods, while at the same time ensuring optimum oxygen conservation.

We claim:

1. A control means for regulating a mixing apparatus which supplies a breathable fluid to a recipient in response to changes in the physiological needs of the recipient, said control means comprising:

means for retaining a reference signal corresponding to the recipient's normal use of oxygen;

adjustment means for changing said reference signal to provide different operational parameters for a recipient;

a housing having a chamber therein and including means for receiving and retaining breathed fluid from the recipient for a predetermined time period to permit the carbon dioxide present in a single exhalation to be averaged with several exhalations and thereby establish a mean carbon dioxide level with respect to the predetermined time period;

sensor means responsive to said mean carbon dioxide level in said chamber for creating a utilization signal corresponding to the recipient's use of oxygen;

computation means connected to said sensor means for combining said reference signal with said utilization signal to develop an output signal;

servomotor means responsive to said output signal for adjusting the mixing apparatus to match the oxygen component in said breathing fluid with that used by the recipient;

means for modifying said output signal to account for changes in the fractional concentration of oxygen in the blood of the recipient due to changes in the minute ventilation associated with an inhalation period of the recipient;

amplifier means responsive to said modified output signal for driving said servomotor in a direction which changes the proportion of oxygen in the breathable fluid communicated from the mixing apparatus to sustain the optimum physiological breathable fluid for said recipient; and indicator means connected to said servomotor for informing an operator of the percentage of oxygen in said breathing fluid supplied to the recipient.

2. The control means, as recited in claim 1 wherein said output signal developed by said computation means represents the inverse ratio of the physiological dead space volume to the tidal volume of the recipient.

* * * * *